United States Patent
Di Capua et al.

(10) Patent No.: US 10,376,440 B2
(45) Date of Patent: Aug. 13, 2019

(54) AUTOMATED VENTILATOR WITH ASSISTED COMPRESSIONS

(71) Applicants: Christopher A. Di Capua, Armonk, NY (US); John F. Di Capua, Jr., Armonk, NY (US)

(72) Inventors: Christopher A. Di Capua, Armonk, NY (US); John F. Di Capua, Jr., Armonk, NY (US)

(*) Notice: Subject to any disclaimer, the term of this patent is extended or adjusted under 35 U.S.C. 154(b) by 0 days.

(21) Appl. No.: 15/069,508

(22) Filed: Mar. 14, 2016

(65) Prior Publication Data

US 2016/0199253 A1    Jul. 14, 2016

Related U.S. Application Data

(63) Continuation of application No. 14/058,365, filed on Oct. 21, 2013, now Pat. No. 9,283,340, which is a (Continued)

(51) Int. Cl.
*A61H 31/00* (2006.01)
*A61M 16/00* (2006.01)
(Continued)

(52) U.S. Cl.
CPC ........... *A61H 31/006* (2013.01); *A61H 31/00* (2013.01); *A61H 31/005* (2013.01); (Continued)

(58) Field of Classification Search
CPC ..... A61H 31/00; A61H 31/005; A61M 16/00; A61M 16/0051
See application file for complete search history.

(56) References Cited

U.S. PATENT DOCUMENTS

| 4,196,725 | A | * | 4/1980 | Gunderson | ........... A61M 16/00 128/205.25 |
| 4,256,100 | A | | 3/1981 | Levy et al. | |

(Continued)

OTHER PUBLICATIONS

Travers, A. H. "Part 4: CPR Overview—2010 American Heart Association Guidelines for Cardiopulmonary Resuscitation and Emergency Cardiovascular Care." Circulation. vol. 122, Nov. 2010 (pp. 676-684).

(Continued)

*Primary Examiner* — Michael J Tsai
*Assistant Examiner* — Christopher E Miller
(74) *Attorney, Agent, or Firm* — Nixon Peabody LLP

(57) ABSTRACT

A system for performing simultaneous ventilation and resuscitation of a patient includes an oxygen source, at least one inspiration control valve, a breathing apparatus, at least one expiration control valve, at least one indicator, and at least one timer. The breathing apparatus is configured to form an air seal with at least a portion of the patient's respiratory tract such that a gas including oxygen can flow from the oxygen source to the lungs. The at least one expiration control valve being configured to selectively actuate an exhalation valve. The at least one indicator for indicating when a rescuer should perform a chest compression. The at least one timer for synchronizing actuation of the at least one inspiration control valve, the at least one expiration control valve, and the indicator, thereby enabling continuous compressions to be provided to the patient while the patient undergoes inspiration and expiration.

3 Claims, 8 Drawing Sheets

Related U.S. Application Data continuation of application No. 13/736,793, filed on Jan. 8, 2013, now Pat. No. 8,631,790.

(60) Provisional application No. 61/748,521, filed on Jan. 3, 2013, provisional application No. 61/731,828, filed on Nov. 30, 2012.

(51) Int. Cl.
*A61M 16/04* (2006.01)
*A61N 1/39* (2006.01)
*A61M 16/20* (2006.01)
*A62B 7/02* (2006.01)
*A61M 16/06* (2006.01)

(52) U.S. Cl.
CPC .......... *A61M 16/022* (2017.08); *A61M 16/04* (2013.01); *A61M 16/0409* (2014.02); *A61M 16/0493* (2014.02); *A61M 16/06* (2013.01); *A61M 16/20* (2013.01); *A61M 16/201* (2014.02); *A61M 16/202* (2014.02); *A61M 16/204* (2014.02); *A61M 16/205* (2014.02); *A61M 16/206* (2014.02); *A61M 16/209* (2014.02); *A61N 1/39* (2013.01); *A62B 7/02* (2013.01); *A61H 2201/107* (2013.01); *A61H 2201/5007* (2013.01); *A61H 2201/5058* (2013.01); *A61H 2201/5071* (2013.01); *A61H 2201/5084* (2013.01); *A61H 2201/5087* (2013.01); *A61M 16/0003* (2014.02); *A61M 2016/0027* (2013.01); *A61M 2202/0208* (2013.01); *A61M 2205/18* (2013.01); *A61M 2205/33* (2013.01); *A61M 2205/3331* (2013.01); *A61M 2205/3334* (2013.01); *A61M 2205/3344* (2013.01); *A61M 2205/581* (2013.01); *A61M 2205/583* (2013.01); *A61M 2205/587* (2013.01); *A61M 2205/80* (2013.01); *A61M 2205/8206* (2013.01); *A61M 2209/06* (2013.01)

(56) References Cited

U.S. PATENT DOCUMENTS

| | | | | |
|---|---|---|---|---|
| 4,297,999 | A | | 11/1981 | Kitrell |
| 4,326,507 | A | | 4/1982 | Barkalow |
| 4,588,383 | A | * | 5/1986 | Parker .................. G09B 23/288 434/265 |
| 4,863,385 | A | * | 9/1989 | Pierce .................. G09B 23/288 434/265 |
| 4,898,174 | A | * | 2/1990 | Fangrow, Jr. ......... A61M 16/00 128/204.24 |
| 5,050,593 | A | * | 9/1991 | Poon ..................... A61M 16/08 128/204.23 |
| 5,301,667 | A | * | 4/1994 | McGrail ............. A61M 16/208 128/205.13 |
| 5,303,699 | A | | 4/1994 | Bonassa |
| RE34,800 | E | * | 11/1994 | Hutchins ................ A61H 31/00 128/898 |
| 5,392,774 | A | | 2/1995 | Sato |
| 5,394,892 | A | * | 3/1995 | Kenny ................... A61H 31/00 128/897 |
| 5,398,676 | A | * | 3/1995 | Press ................ A61M 16/0051 128/204.18 |
| 5,496,257 | A | * | 3/1996 | Kelly ................... A61H 31/005 600/454 |
| 5,540,220 | A | * | 7/1996 | Gropper ............. A61M 16/024 128/204.21 |
| 5,551,420 | A | | 9/1996 | Lurie et al. |
| 5,692,498 | A | | 12/1997 | Lurie et al. |
| 5,806,512 | A | | 9/1998 | Abramov et al. |
| 6,030,353 | A | * | 2/2000 | Van Brunt ........... A61H 9/0078 239/431 |
| 6,055,981 | A | | 5/2000 | Laswick et al. |
| 6,152,135 | A | * | 11/2000 | DeVries ................ A61M 16/00 128/204.18 |
| 6,155,257 | A | * | 12/2000 | Lurie ................... A61H 31/005 128/204.18 |
| 6,289,890 | B1 | * | 9/2001 | Bliss ..................... A61M 16/00 128/203.11 |
| 6,374,827 | B1 | | 4/2002 | Bowden et al. |
| 7,174,891 | B2 | | 2/2007 | Lurie et al. |
| 7,190,999 | B2 | * | 3/2007 | Geheb ...................... A61B 5/11 600/515 |
| 7,220,235 | B2 | | 5/2007 | Geheb et al. |
| 7,980,244 | B2 | * | 7/2011 | Boone ............... A61M 16/0051 128/200.24 |
| 8,376,973 | B2 | | 2/2013 | Flood |
| 9,352,115 | B1 | * | 5/2016 | DeStefano ............ A61M 16/20 |
| 2003/0172935 | A1 | | 9/2003 | Miller |
| 2004/0103896 | A1 | | 6/2004 | Jafari |
| 2005/0085799 | A1 | | 4/2005 | Luria et al. |
| 2005/0092324 | A1 | * | 5/2005 | Bowden ............... A61H 31/005 128/204.21 |
| 2005/0126578 | A1 | | 6/2005 | Garrison et al. |
| 2005/0165334 | A1 | * | 7/2005 | Lurie .................... A61M 16/06 601/44 |
| 2008/0145827 | A1 | | 6/2008 | Strand et al. |
| 2009/0062701 | A1 | * | 3/2009 | Yannopoulos ....... A61H 9/0078 601/41 |
| 2010/0114220 | A1 | | 5/2010 | Paradis |
| 2010/0160839 | A1 | * | 6/2010 | Freeman ................ A61H 31/00 601/41 |
| 2010/0326442 | A1 | | 12/2010 | Hamilton et al. |
| 2010/0326443 | A1 | * | 12/2010 | Steen .................... A61M 16/04 128/204.23 |
| 2011/0098611 | A1 | | 4/2011 | Flood |
| 2011/0172572 | A1 | | 7/2011 | Belalcazar |
| 2011/0201979 | A1 | * | 8/2011 | Voss ..................... A61H 31/005 601/41 |
| 2011/0236867 | A1 | | 9/2011 | Stickney et al. |
| 2011/0301512 | A1 | * | 12/2011 | Olson .................. A61H 31/005 601/41 |
| 2012/0016179 | A1 | | 1/2012 | Paradis |

OTHER PUBLICATIONS

Roger, V. L. et al. "Executive Summary: Heart Diseases and Stroke Statistics—2012 Update—A Report from the American Heart Association." Circulation. vol. 125, No. 1, Jan. 2012 (pp. 188-197).

Garza, A. G. "Improved Patient Survival Using a Modified Resuscitation Protocol for Out-of-Hospital Cardiac Arrest." Circulation. vol. 119, No. 19, May 2009 (pp. 2597-2605).

Sayre, M. R. et al. "Hands-Only (Compression-Only) Cardiopulmonary Resuscitation: A Call to Action for Bystander Response to Adults Who Experience Out-of-Hospital Sudden Cardiac Arrest—A Science Advisory for the Public From the American Heart Association Emergency Cardiovascular Care Committee." Circulation. vol. 117, No. 16, Apr. 2008 (pp. 2162-2167).

"Part 4: Adult Basic Life Support." Circulation. vol. 112, Dec. 2005 (pp. 19-34).

Brooks, S. C. et al. "Devices Used in Cardiac Arrest." Emergency Medical Clinics of North America. vol. 30, No. 1, Feb. 2012 (pp. 179-193).

Field, J. M. "Part 1: Executive Summary—2010 American Heart Association Guidelines for Cardiopulmonary Resuscitation and Emergency Cardiovascular Care." Circulation. vol. 122, Nov. 2010 (pp. 640-656).

Berg, R. A. "Part 5: Adult Basic Life Support—2010 American Heart Association Guidelines for Cardiopulmonary Resuscitation and Emergency Cardiovascular Care." Circulation. vol. 122, Nov. 2010 (pp. 685-705).

Locke, C. J. et al. "Bystander Cardiopulmonary Resuscitation—Concerns About Mouth-to-Mouth Contact." Archives of Internal Medicine. vol. 155, No. 9, May 1995 (pp. 938-943).

(56) References Cited

OTHER PUBLICATIONS

Ornato, J. P. "Attitudes of BCLS Instructors About Mouth-to-Mouth Resuscitation During the AIDS Epidemic." Annals of Emergency Medicine. vol. 19, No. 2, Feb. 1990 (pp. 151-156).
Brenner, B. E. "Reluctance of Internists and Medical Nurses to Perform Mouth-to-Mouth Resuscitation." Archives of Internal Medicine. vol. 153, No. 15, Aug. 1993 (pp. 1763-1769).
Brenner, B. et al. "The Reluctance of House Staff to Perform Mouth-to-Mouth Resuscitation in the Inpatient Setting: What are the Considerations?" Resuscitation. vol. 28, No. 3, Dec. 1994 (pp. 185-193).
Brenner, B. E. et al. "Determinants of Reluctance to Perform CPR Among Residents and Applicants: The Impact of Experience on Helping Behavior." Resuscitation. vol. 35, No. 3, Nov. 1997 (pp. 203-211).
Hew, P. et al. "Reluctance of Paramedics and Emergency Medical Technicians to Perform Mouth-to-Mouth Resuscitation." The Journal of Emergency Medicine. vol. 15, No. 3, May 1997 (pp. 279-284).
Mejicano, G. C. "Infections Acquired During Cardiopulmonary Resuscitation: Estimating the Risk and Defining Strategies for Prevention." Annals of Internal Medicine. vol. 129, No. 10, Nov. 1998 (pp. 813-828).
Simmons, M. et al. "Bench Evaluation: Three Face-Shield CPR Barrier Devices." Respiratory Care. vol. 40, No. 6, Jun. 1995 (pp. 618-623).
Axelsson, A. et al. "Attitudes of Trained Swedish Lay Rescuers Toward CPR Performance in an Emergency. A Survey of 1012 Recently Trained CPR Rescuers." Resuscitation. vol. 44, No. 1, Mar. 2000 (pp. 27-36).
Kliegel, A. et al. "The Attitudes of Cardiac Arrest Survivors and their Family Members Towards CPR Courses." Resuscitation. vol. 47, No. 2, Oct. 2000 (pp. 147-157).
Melanson, S. W. et al. "EMS Provider Reluctance to Perform Mouth-to-Mouth Resuscitation." Prehospital Emergency Care. vol. 4, No. 1, Jan. 2000 (pp. 48-52).
Shibata, K. et al. "Obstacles to Bystander Cardiopulmonary Resuscitation in Japan." Resuscitation. vol. 44, No. 3, May 2000 (pp. 187-193).
Boucek, C. D. "Willingness to Perform Mouth-to-Mouth Ventilation by Health Care Providers: A Survey." Resuscitation. vol. 80, No. 8, Aug. 2009 (pp. 849-853).
Makinen, M. et al. "Assessment of CPR-D Skills of Nursing Students in Two Institutions: Reality Versus Recommendations in the Guidelines." European Journal of Emergency Medicine. vol. 17, No. 4, Aug. 2010 (pp. 237-239).
Makinen, M. et al. "Nurses' Attitudes Towards Resuscitation and National Resuscitation Guidelines—Nurses Hesitate to Start CPR-D." Resuscitation. vol. 80, No. 12, Dec. 2009 (pp. 1399-1404).
Walker, G. M. et al. "Prolonged Two-Man Basic Life Support May Result in Hypocarbia in the Ventilating Rescuer." Resuscitation. vol. 50, No. 2, Aug. 2001 (pp. 179-183).
Idris, A. H. et al. "Does Hypoxia or Hypercarbia Independently Affect Resuscitation from Cardiac Arrest?" Chest. vol. 108, No. 2, Aug. 1995 (pp. 522-528).
Ramaraj, R. et al. "Rationale for Continuous Chest Compression Cardiopulmonary Resuscitation." Heart. vol. 95, No. 24, Dec. 2009 (pp. 1978-1982).
Eisenburger, P. et al. "Gas Concentrations in Expired Air During Basic Life Support Using Different Ratios of Compression to Ventilation." Resuscitation. vol. 73, No. 1, Apr. 2007 (pp. 115-122).
Neumar, R. W. "Part 8: Adult Advanced Cardiovascular Life Support—2010 American Heart Association Guidelines for Cardiopulmonary Resuscitation and Emergency Cardiovascular Care." Circulation. vol. 122, Nov. 2010 (pp. 729-767).
Martin, P. D. et al. "Training Nursing Staff in Airway Management for Resuscitation." Anaesthesia. vol. 48, No. 1, Jan. 1993 (pp. 33-37).
Murray, M. J. "Evaluation of Prehospital Insertion of the Laryngeal Mask Airway by Primary Care Paramedics with Only Classroom Mannequin Training." Canadian Journal of Emergency Medicine. vol. 4, No. 5, Sep. 2002 (pp. 338-343).
Alexander, R. et al. "Mouth to Mouth Ventilation: A Comparison of the Laryngeal Mask Airway with Laerdal Pocket Facemask." Resuscitation. vol. 80, No. 11, Nov. 2009 (pp. 1240-1243).
Nagao et al. "Comparison of Arterial Blood Gases of Laryngeal Mask Airway and Bag-Valve-Mask Ventilation in Out-of-Hospital Cardiac Arrest." Circulation Journal. vol. 73, No. 6, Mar. 2009 (pp. 490-496).
Heuer, J. F. et al. "Initial Ventilation Through Laryngeal Tube Instead of Face Mask in Out-of-Hospital Cardiopulmonary Arrest is Effective and Safe." European Journal of Emergency Medicine. vol. 17, No. 1, Feb. 2010 (pp. 10-15).
Howes, B. W. et al. "LMA Supreme™ Insertion by Novices in Manikins and Patients." Anaesthesia. vol. 65, No. 4, Apr. 2010 (pp. 343-347).
Timmermann, A. et al. "Laryngoscopic Versus Intubating LMA Guided Tracheal Intubation by Novice Users—A Manikin Study." Resuscitation. vol. 73, No. 3, Jun. 2007 (pp. 412-416).
Wharton, N. M. "I-gel Insertion by Novices in Manikins and Patients." Anaesthesia. vol. 63, No. 9, Sep. 2008 (pp. 991-995).
Weksler, N. et al. "Insertion of the Endotracheal Tube, Laryngeal Mask Airway and Oesophageal-Tracheal Combitube®. A 6-month Comparative Prospective Study of Acquistion and Retention Skills by Medical Students." European Journal of Anaesthesiology. vol. 22, No. 5, May 2005 (pp. 337-340).
Pennant, J. H. "Comparison of the Endotracheal Tube and Laryngeal Mask in Airway Management by Paramedical Personnel." Anesthesia and Analgesia. vol. 74, No. 4, Apr. 1992 (pp. 531-534).
Dorges, V. et al. "Comparison of Different Airway Management Strategies to Ventilate Apneic, Nonpreoxygenated Patients." Critical Care Medicine. vol. 31, No. 3, Mar. 2003 (pp. 800-804).
Rumball, C. J. "The PTL, Combitube, Laryngeal Mask, and Oral Airway: A Randomized Prehospital Comparative Study of Ventilatory Device Effectiveness and Cost-effectiveness in 470 Cases of Cardiorespiratory Arrest." Prehospital Emergency Care. vol. 1, No. 1, Jan. 1997 (pp. 1-10).
Stone, B. J. et al. "The Incidence of Regurgitation During Cardiopulmonary Resuscitation: A Comparison Between the Bag Valve Mask and Laryngeal Mask Airway." Resuscitation. vol. 38, No. 1, Jul. 1998 (pp. 3-6).
Alexander, R. et al. "A Comparison of the Laryngeal Mask Airway and Guedel Airway, Bag and Facemask for Manual Ventilation Following Formal Training." Anaesthesia. vol. 48, No. 3, Mar. 1993 (pp. 231-234).
Berg, R. "Role of Mouth-to-Mouth Rescue Breathing in Bystander Cardiopulmonary Resuscitation for Asphyxial Cardiac Arrest." Critical Care Medicine. vol. 28, No. 11, Nov. 2000 (pp. 193-195).
Choi, H. J. et al. "Effectiveness of Mouth-to-Mouth Ventilation After Video Self-Instruction Training in Laypersons." American Journal of Emergency Medicine. vol. 28, No. 6, Jul. 2010 (pp. 654-657).
Wik, L. et al. "Quality of Cardiopulmonary Resuscitation During Out-of-Hospital Cardiac Arrest." Journal of American Medical Association. vol. 293, No. 3, Jan. 2005 (pp. 299-304).
Iwami, T. et al. "Chest Compression-Only Cardiopulmonary Resuscitation for Out-of-Hospital Cardiac Arrest with Public-Access Defibrillation." Circulation. vol. 126, No. 24, Dec. 2012 (pp. 2844-2851).
Cunningham, L. M. et al. "Cardiopulmonary Resuscitation for Cardiac Arrest: the Important of Uninterrupted Chest Compressions in Cardiac Arrest Resuscitation." American Journal of Emergency Medicine. vol. 30, No. 8, Oct. 2012 (pp. 1630-1638).
Xanthos, T. et al. "Continuous Chest Compressions Improve Survival and Neurologic Outcome in a Swine Model of Prolonged Ventricular Fibrillation." American Journal of Emergency Medicine. vol. 30, No. 8, Oct. 2012 (pp. 1389-1394).
Iglesias, J. M. et al. "Chest Compressions Versus Ventilation Plus Chest Compressions in a Pediatric Asphyxial Cardiac Arrest Animal Model." Intensive Care Medicine. vol. 36, No. 4, Apr. 2010 (pp. 712-716).
Sanders, A. B. et al. "Survival and Neurologic Outcome After Cardiopulmonary Resuscitation with Four Difference Chest Com-

(56) References Cited

OTHER PUBLICATIONS pression-Ventilation Ratios." Annals of Emergency Medicine. vol. 40, No. 6, Dec. 2002 (pp. 553-562).
Wang, S. et al. "Relationship Between Intrathoracic Pressure and Hemodynamics During Cardiopulmonary Resuscitation in a Porcine Model of Prolonged Cardiac Arrest." Chinese Medical Journal. vol. 125, No. 20, Oct. 2012 (pp. 3606-3611).
Hall, J. E. "Chapter 37: Pulmonary Ventilation." Guyton and Hall Textbook of Medical Physiology; Elsevier Health Sciences, Philadelphia, PA (pp. 465-475).
West, J. B. "Chapter 2: Ventilation: How Gas Gets to the Alveoli." Respiratory Physiology, The Essentials; Lippincott Williams & Wilkins, Baltimore, MD (pp. 12-23).
Theiler, L. et al. "i-gel™ Supraglottic Airway in Clinical Practice: A Prosepective Observational Multicentre Study." British Journal of Anaesthesia. vol. 109, No. 6, Sep. 2012 (pp. 990-995).
Jorgenson, D. B. et al. "Impacting Sudden Cardiac Arrest in the Home: A Safety and Effectiveness Study of Privately-Owned AEDs." Resuscitation. vol. 84, No. 2, Oct. 2012 (pp. 149-153).
Jorgenson, D. B. et al. "AED Use in Business, Public Facilities and Homes by Minimally Trained First Responders." Resuscitation. vol. 59, No. 2, Nov. 2003 (pp. 225-233).
International Search Report and Written Opinion dated Mar. 7, 2014 which issued in corresponding International Patent Application No. PCT/US2013/069186 (12 pages).

\* cited by examiner

AUTOMATED VENTILATOR WITH ASSISTED COMPRESSIONS

CROSS-REFERENCE TO RELATED APPLICATIONS

This application is a continuation of U.S. patent application Ser. No. 14/058,365, filed Oct. 21, 2013, now allowed, which is a continuation of U.S. patent application Ser. No. 13/736,793, filed Jan. 8, 2013, now U.S. Pat. No. 8,631,790, which claims the benefit of U.S. Provisional Patent Application 61/748,521, filed Jan. 3, 2013, and of U.S. Provisional Patent Application 61/731,828, filed Nov. 30, 2012, all of which are hereby incorporated by reference in their entireties.

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

Aspects of the present disclosure relate to ventilators, and more particularly, to an automated ventilator with assisted compressions.

BACKGROUND OF THE INVENTION

Sudden cardiac arrest is the leading cause of death in the United States and Canada and accounts for one in every six deaths. The Centers for Disease Control and Prevention estimate that approximately 405,000 people annually in the United States die from coronary heart disease. About 250,000 of these deaths occur outside of a hospital setting. Achieving high survival rates depends upon a public that is well trained in Cardiopulmonary Resuscitation ("CPR") because arrival of emergency medical services typically takes longer than five minutes, but irreversible brain damage predictably develops after only four minutes of cardiac arrest.

CPR is a procedure performed on a patient undergoing cardiac arrest. CPR includes compression of the patient's chest by a rescuer (alternatively "resuscitator") and can be performed with or without ventilating the patient. The chest compressions are performed to create artificial blood flow in a patient. The rescuer repeatedly compresses the patient's chest in order to manually pump blood through the patient's heart so that blood continues to circulate to the patient's vital organs. These compressions should occur at a rate of 100 or more compressions per minute. Providing fewer than 100 compressions per minute decreases effectiveness of CPR. A problem arises when the lay public does not know or does not recall the desired rate of compressions. What is more, even if the rescuer knows the desired rate, it is difficult to maintain a consistent compression rate without assistance. Further, CPR without ventilation is less effective than CPR with ventilation because oxygen saturation falls. This drop in oxygen decreases patient survival after four to six minutes of compression-only CPR.

Mouth-To-Mouth Ventilation ("MTMV") CPR is the current standard for treating out-of-hospital cardiac arrest. During MTMV CPR, the rescuer performs chest compressions for a period of time, and then stops the compressions and attempts to ventilate the patient. During ventilation, the rescuer tilts the patient's head back, lifts the chin, pinches the patient's nose, creates an air seal between the patient's mouth and the rescuer's mouth, and provides two rescue breaths by exhaling into the patient's mouth. Typically, the ratio is thirty compressions to two breaths. MTMV CPR has several limitations including: (1) rescuer fear of disease transference from the patient; (2) interruption of chest compressions in order to ventilate the patient; (3) inadequate volumes of gas exhaled by the rescuer into the patient's lungs; and (4) ineffective ventilation due to utilization of the rescuer's expired gasses which are only about 15% oxygen.

MTMV CPR remains the current standard in airway management utilized by the lay public; however, the lay public has demonstrated consistent difficulty and hesitation in performing standard MTMV CPR. Studies illustrate that MTMV CPR is often performed incorrectly, resulting in inadequate ventilation. For example, missing or poorly performing any ventilation steps results in ineffective ventilation. Because of this, patients have better outcomes when bystanders perform CPR without attempting to ventilate the patient. Moreover, ventilation effectiveness is inherently limited by utilizing the rescuer's expired gases because the fraction of inspired oxygen ("$FiO_2$") is only about 15%. Further, even if the rescuer properly performs each step in MTMV CPR, blood flow in the patient is hindered because the rescuer must interrupt the process of chest compressions.

Alternatives to MTMV CPR include CPR using Bag-Valve-Mask ventilation, endotracheal intubation, and Laryngeal Mask Airway ventilation. These devices are not typically available to the lay public when performing CPR and some can even endanger the patient if used incorrectly, e.g., by the lay public. A bag-valve-mask uses a mask to create the air seal over the patient's mouth and nose. A bag is then compressed by hand in order to force atmospheric air, which is 21% oxygen, into the patient's lungs. Pressure-sensitive valves on the bag-valve-mask control the direction of airflow. Use of the bag-valve-mask still hinders blood flow in the patient because the rescuer must interrupt chest compressions in order to ventilate the patient.

Endotracheal intubation involves inserting a tube through the patient's mouth and into the trachea. The patient is ventilated by a bag-valve placed on the exposed end of the tube or the rescuer exhaling into the exposed end. Endotracheal intubation is an advanced procedure that involves slow insertion times and has been shown to have a failure rate in excess of 30%. Further, use of endotracheal intubation still hinders blood flow in the patient because the rescuer must interrupt chest compressions in order to ventilate the patient.

Laryngeal Mask Airway ("LMA") ventilation involves inserting a device such as an I-GEL® supraglottic airway device with a soft, gel-like, non-inflatable cuff (Intersurgical Ltd., Wokingham, Berkshire, UK) into the patient's mouth for positive pressure ventilation. The I-GEL® supraglottic airway device is positioned in the supraglottic airway of the patient to deliver air to the patient's lungs. The patient is ventilated by a bag-valve placed on the exposed end of the I-GEL® airway device or by the rescuer exhaling into the exposed end. Use of the I-GEL® supraglottic airway device still hinders blood flow in the patient because the rescuer must interrupt chest compressions in order to ventilate the patient.

In the case of out-of-hospital cardiac arrest, the current survival rate is 7.6%. As a result, the AMERICAN HEART ASSOCIATION® (American Heart Association, Inc., Dallas, Tex.) ("AHA") has called for research regarding alternative methods of CPR. Thus, it would be desirable to develop a system that overcomes the problems and limitations associated with traditional methods of CPR to increase rates of survival for patients suffering from cardiac arrest.

SUMMARY OF THE INVENTION

According to one aspect of the present invention, a system for performing simultaneous ventilation and resuscitation of a patient includes an oxygen source, at least one inspiration control valve, a breathing apparatus, at least one expiration control valve, at least one indicator, and at least one timer. The at least one inspiration control valve may be disposed between the oxygen source and the patient. The breathing apparatus may be disposed downstream from the inspiration control valve and may be configured to form an air seal with at least a portion of the patient's respiratory tract such that a gas including oxygen can flow from the oxygen source to the lungs. The at least one expiration control valve may be configured to selectively actuate an exhalation valve. The at least one indicator is for indicating when a rescuer should perform a chest compression, and the at least one indicator indicates continuously at a regular timed or periodic interval (e.g., at a frequency of 100 indications per minute) simultaneously with the actuation of the inspiration and expiration control valves. The at least one timer is for synchronizing actuation of the at least one inspiration control valve, the at least one expiration control valve, and the indicator, thereby enabling continuous compressions to be provided to the patient as guided by the continuous periodic indications produced by the indicator while the patient undergoes inspiration and expiration.

According to another aspect of the present invention, a kit of components for assisting in resuscitation of a patient includes an indicator, a timer, and an Automatic External Defibrillator ("AED"). The indicator is configured to indicate when a rescuer should perform a chest compression, and the indicator produces audible or visual indications continuously at a regular timed or periodic interval (such as at a frequency of 100 times per minute) simultaneously with the operation of the AED during an attempted revival of a human patient. The timer is for actuating the indicator at predetermined intervals.

According to yet another aspect of the present invention, a system for performing automated ventilation with continuous chest compressions of a patient includes an oxygen source, at least one inspiration control valve, a breathing apparatus, an expiration control valve, at least one timer, and a switch. The at least one inspiration control valve may be disposed between the oxygen source and the patient. The breathing apparatus may be disposed downstream from the inspiration control valve, the breathing apparatus configured to form a hermetic or substantially air-tight seal with at least a portion of the patient's respiratory tract such that a gas including oxygen can flow from the oxygen source to the lungs. The expiration control valve may be configured to selectively actuate an exhalation valve. The at least one timer is for synchronizing the actuation of the at least one inspiration control valve and the expiration control valve. The switch is for activating the at least one timer. In response to activating the switch, the at least one timer is configured to selectively actuate the at least one inspiration control valve and the expiration control valve according to predetermined settings.

Optionally, an indicator can produce an audible or visual indication continuously at a regular timed or periodic interval simultaneously with the selective actuation operation of the inspiration and expiration control valves.

DETAILED DESCRIPTION

During chest compressions, the downward thrust portion of the compression increases intrathoracic pressure and pushes blood out of the heart. This circulates blood throughout the body. After the thrust portion, the chest decompresses and negative pressure is created in the intrathoracic cavity. This decompression pulls venous blood into the heart so that the subsequent chest compression will continue to circulate blood. If positive-pressure ventilation occurs during the decompression phase, the negative pressure in the intrathoracic cavity is diminished. This reduces the amount of venous blood that returns to the heart and decreases effectiveness of the compressions. Therefore, some aspects disclosed herein are designed to deliver positive-pressure ventilation during the downward compression phase and to leave the decompression phase substantially uninhibited.

Further, aspects of the present disclosure help the lay public perform resuscitation by replacing difficult to teach MTMV CPR with systems and methods that are easy to use and that perform continuous, automatic ventilation while allowing the rescuer to concentrate on chest compressions so that continuous blood flow and delivery of oxygen is maintained to vital organs.

Figure 1:
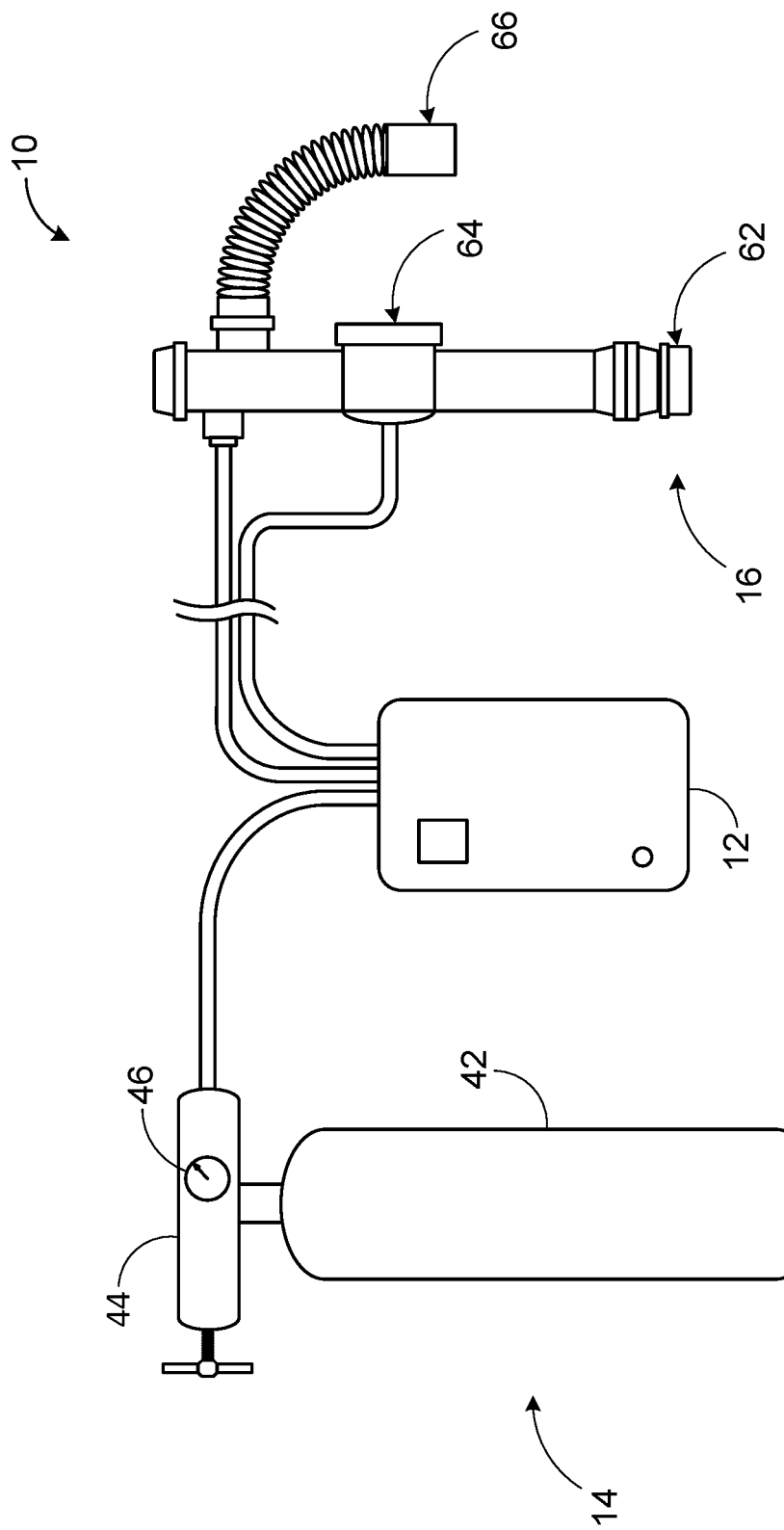
FIG. 1 is a top view of a system for automated ventilation and assisted compression of a patient, according to an aspect of the present invention.

FIG. 1 illustrates a system for automated ventilation and assisted compression of a patient according to an aspect of the present invention. The system 10 includes a control box 12, a gas source 14, and a breathing apparatus 16. As will be described in more detail with reference to FIGS. 2-4, the control box 12 includes timers, a battery, inspiration and expiration control valves, and indicators. The control box 12 synchronizes and controls indicators for chest compressions and flow of gas through system 10. The gas source 14 includes a tank 42 of compressed oxygen, a supply regulator 44, and a pressure gauge 46. The supply regulator 44 receives gas from the tank 42 and reduces the pressure to provide a substantially constant output pressure to the system 10. In one non-limiting example, the supply regulator 44 reduces the pressure from about 3,000 psi to about 50 psi. The pressure gauge 46 is disposed upstream of the supply regulator 44 to indicate the pressure of gas remaining in the tank 42. It is contemplated that a pressure gauge may be disposed downstream from the supply regulator 44 to indicate the pressure received by the system 10. It is further contemplated that only a downstream pressure gauge may be used. The breathing apparatus 16 includes a relief valve 62, an exhalation valve 64, and a connector 66. The breathing apparatus 16 is configured such that gas may flow between the relief valve 62, the exhalation valve 64, and the connector 66. The relief valve 62 may be a spring-loaded valve that actuates when the pressure inside of the breathing apparatus 16 reaches a predetermined threshold. The exhalation valve 64 may be a one-way valve that allows air to flow from the breathing apparatus 16 to atmosphere during exhalation. The connector 64 is configured to interface with a ventilating device such as an LMA or respiratory mask.

Figure 2A:
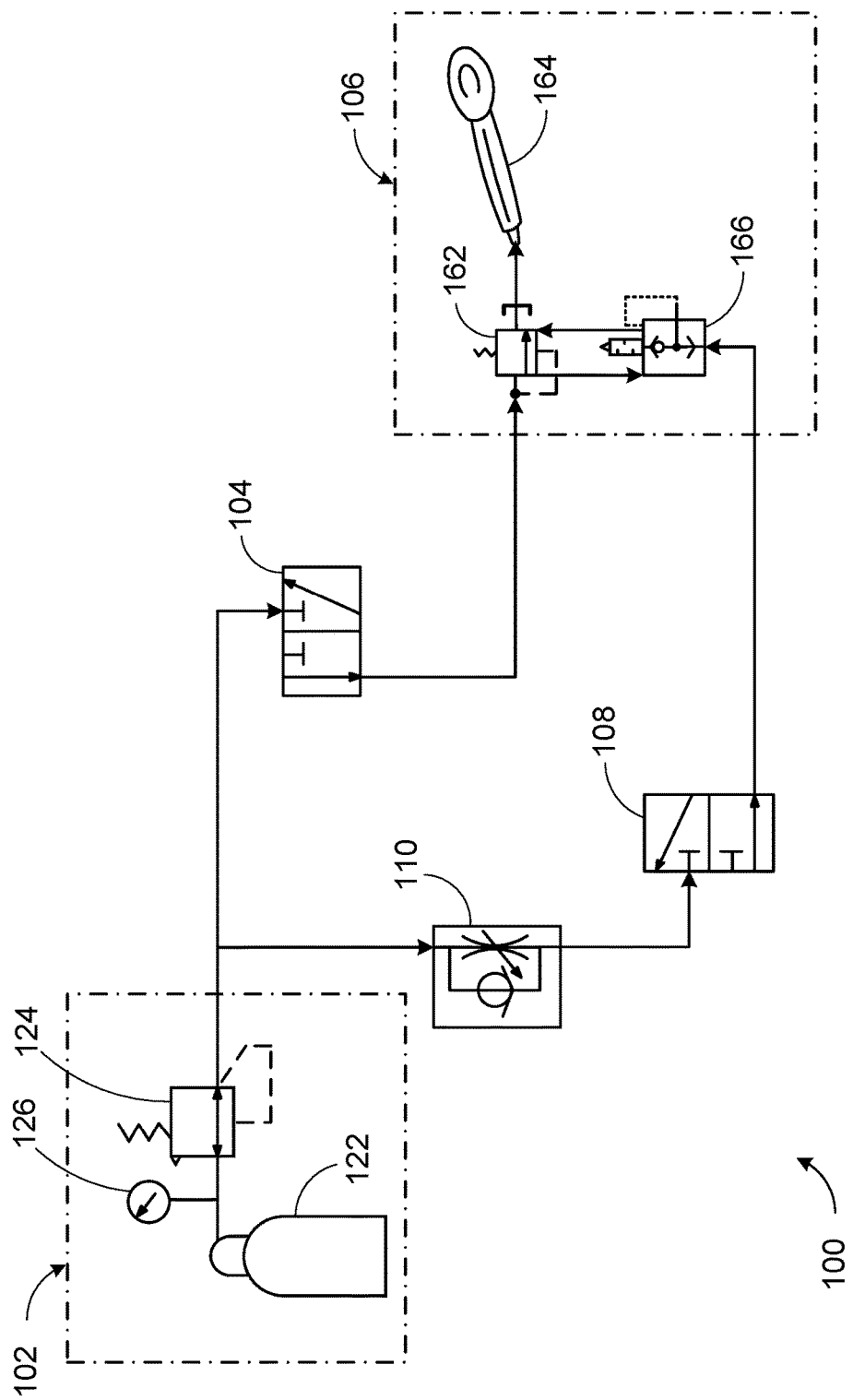
FIG. 2A is a schematic view of a system for automated ventilation of a patient during an inspiratory cycle, according to an aspect of the present invention.
Figure 2B:
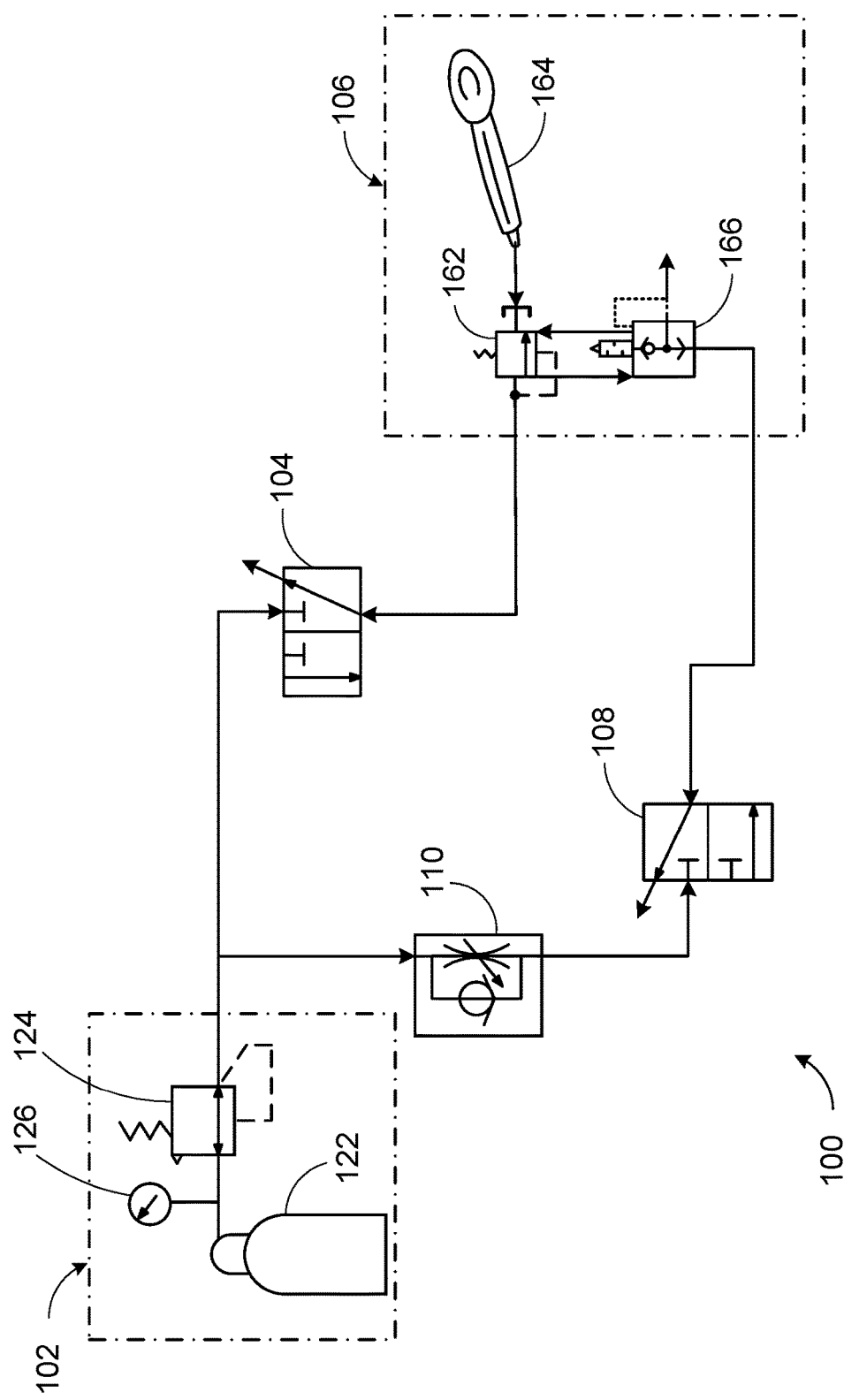
FIG. 2B is a schematic view of the system of FIG. 1A during an expiratory cycle, according to an aspect of the present invention.

Referring now to FIGS. 2A and 2B, a schematic of a system for automated ventilation of a patient is shown. The system includes a gas source 102, two inspiration control valves 104, a breathing apparatus 106, an expiration control valve 108, and a flow control valve 110. The gas source 102 is connected to the two inspiration control valves 104 and the expiration control valve 108. The flow control valve 110 is disposed in the flow path between the gas source 102 and the expiration control valve 108.

The gas source 102 includes a pressurized oxygen tank 122, a supply regulator 124, and a pressure gauge 126. The pressurized oxygen tank 122 stores substantially pure oxygen under pressure. The pressure of oxygen within the oxygen tank 122 drops during use because gas is supplied to the system but not returned to the tank. In one aspect, a medical-grade compressed-oxygen cylinder is used such as a LUXFER® model M09B (Luxfer Medical, Riverside, Calif.) ("the M09B") carbon fiber compressed oxygen cylinder. Carbon fiber oxygen tanks are generally lighter than standard aluminum or steel medical grade oxygen cylinders. Further, carbon fiber coated cylinders can utilize higher service pressures than standard cylinders including a pressure of about 3,000 psi. The M09B loaded to about 3,000 psi desirably includes enough oxygen to supply to the system for more than one hour of continuous use. These characteristics add to the portability of the system and make the system more compact.

The supply regulator 124 is disposed downstream of the oxygen tank 122 and controls the pressure of gas supplied to the system by the pressurized oxygen tank 122. The pressure after the supply regulator 124 is lower than the pressure of the oxygen tank 122 and remains substantially constant despite varying pressure in the oxygen tank 122. In one aspect, a portable, Emergency Medical Service grade regulator such as the GENTEC® 286MB-25LY (Gentec Corporation, Shanghai, China) may be used to lower the tank pressure to, for example, about 50 psi. The pressure gauge 126 is disposed upstream of the supply regulator 124 and provides a pressure reading of the oxygen tank 122.

The two inspiration control valves 104 are disposed downstream of the gas source 102. In one aspect, the inspiration control valves 104 are three-port, two-condition solenoids having an OFF state and an ON state. The inspiration control valves 104 are normally in the OFF state. When in the OFF state, the inspiration control valves 104 prevent the flow of gas from the gas source 102 and vent gas from the breathing apparatus 106. When in the ON state, the inspiration control valves 104 are actuated and allow gas to flow from the gas source 102 toward the breathing apparatus 106. In one aspect, the inspiration control valves 104 are CLIPPARD® MINIMATIC® E315F-2W012 (Clippard Instrument Co., Cincinnati, Ohio) solenoid valves. The CLIPPARD® MINIMATIC® E315F-2W012 solenoid valves are generally small and lightweight with a rapid activation time of approximately 10ms. In one aspect, the inspiration control valves 104 are placed on a double manifold such as the CLIPPARD® MINIMATIC® E315M-02 (Clippard Instrument Co., Cincinnati, Ohio). Two inspiration control valves 104 are used to increase oxygen supply flow-rate for inspiration while maintaining a rapid response time and a low peak inspiratory pressure. In one experiment, using a single inspiratory valve resulted in a peak inspiratory pressure above 26 cm $H_2O$, but using two inspiratory valves resulted in a peak inspiratory pressure below 26 cm $H_2O$. As used herein, measurements in cm $H_2O$ are relative to atmospheric pressure. It is contemplated that more or fewer than two inspiration control valves 104 may be used. It is further contemplated that different types of solenoids can be used.

The breathing apparatus 106 includes a pressure relief valve 162, an I-GEL® supraglottic airway device 164, and an exhalation valve 166. The pressure relief valve 162 is located downstream from the inspiration control valves 104 and upstream from the I-GEL® supraglottic airway device 164. The pressure relief valve 162 is configured to actuate and release gas from the system if pressure at the valve increases past a predetermined threshold. This can minimize the risk of lung injury and gastric distention by helping to ensure that peak inspiratory pressures do not exceed predetermined limits. For example, delivering a breath with a pressure of about 50 psi during a single chest compression results in high peak inspiratory pressures. If the relief valve 162 is configured to actuate at, for example, approximately 23 cm H2O, the system can be safely utilized on patients with a wide variety of lung sizes, body physiques, ages, and the like. In one aspect, the pressure relief valve 162 is the ALLEGIANCE® 2K8082 (Allegiance Corporation, McGaw Park, IL). As will be described more in relation to FIG. 2 below, the I-GEL® supraglottic airway device 164 is configured to be inserted into the mouth of the patient and transfer gas between the lungs of the patient and the system.

The exhalation valve 166 is a one-way valve that allows gas to flow from the I-GEL® supraglottic airway device 164 to the expiration control valve 108. The exhalation valve 166 is configured to allow gas expelled from the lungs of the patient to escape the system. In one aspect, the exhalation valve 166 is a low-resistance, mushroom-style valve such as a 2018 from BIO-MED DEVICES® (Bio-Med Devices, Guilford, CT). It is contemplated that other types of valves may also be used.

The expiration control valve 108 is used to control the operation of the exhalation valve 166. In one aspect, the expiration control valve 108 is a three-port, two-condition solenoid having an OFF state and an ON state. The expiration control valve 108 is normally in the OFF state. When in the OFF state, the expiration control valve 108 prevents the flow of gas from the gas source 102 and vents gas to depressurize the exhalation valve 166. When in the ON state, the expiration control valve 108 is actuated and allows gas to flow from the gas source 102 to the exhalation valve 166. In one aspect, the expiration control valve 108 is a CLIPPARD® MINIMATIC® E315F-2W012 as described above.

The flow control valve 110 is disposed between the supply regulator 124 and expiration control valve 108. The flow control valve 110 lowers the pressure that the exhalation valve 166 is exposed to. In one aspect, the flow control valve 110 lowers the pressure to about 26 cm H₂O, the working pressure of the exhalation valve 166.

Figure 3:
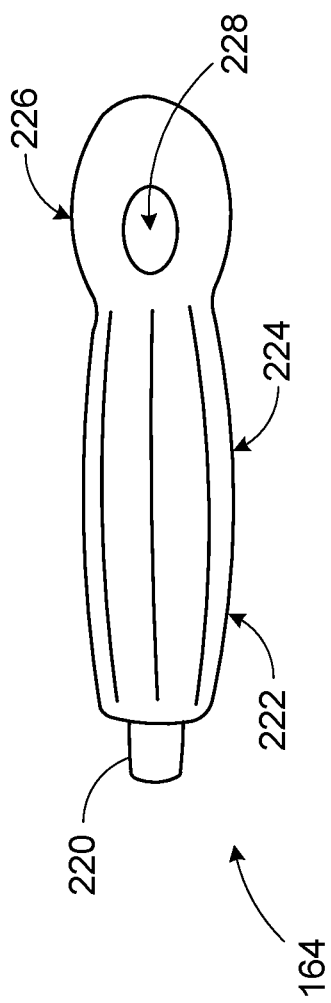
FIG. 3 is a top view of an I-GEL® supraglottic airway device.

Referring now to FIG. 3 an I-GEL® supraglottic airway device 164 is shown. The I-GEL® supraglottic airway device 164 includes a connector 220, a bite block 222, a gastric vent 224, and a cuff 226. The cuff 226 defines an aperture 228 that runs to the connector 220 and is configured to transfer gasses into and out of the lungs of the patient. The connector 220 is configured to interface with a gas supply such as a bag-valve. Alternatively, a rescuer may exhale gasses directly into the connector 220. The bite block 222 is a semi-rigid portion of the I-GEL® supraglottic airway device 164 that prevents the aperture 228 from collapsing if the patient bites down. The cuff 226 forms an air or substantially hermetic seal in the patient's supraglottic area such that gasses passed through the aperture 228 enter the lungs. In some aspects, the air seal is airtight or substantially airtight and inhibits or prevents air from moving into or out of the patient's lung(s) unless it travels through a predetermined path such as, for example, the aperture 228. In other aspects, the air seal is not entirely airtight and allows some air to pass. Put another way, even though the air seal may not be completely airtight, the air seal is such that the patient's lung(s) can still receive adequate oxygenation.

Advantageously, the I-GEL® supraglottic airway device 164 can be inserted blindly into a patient's mouth. When correctly positioned, the I-GEL® supraglottic airway device 164 can be used to deliver positive pressure ventilation by using, for example, a bag-valve. Use of the I-GEL® supraglottic airway device 164 helps prevent transfer of body fluids between the rescuer and the patient when compared with MTMV CPR. Further, proper use of the I-GEL® supraglottic airway device 164 is relatively easily taught. In fact, the American Heart Association has added the use of LMAs such as the I-GEL® supraglottic airway device 164 into both the basic CPR and Advanced Cardiovascular Life Support protocols as an alternative to MTMV CPR. What is more, the I-GEL® supraglottic airway device 164 advantageously secures the airway more consistently and quickly than other methods of ventilation discussed above.

Figure 4:
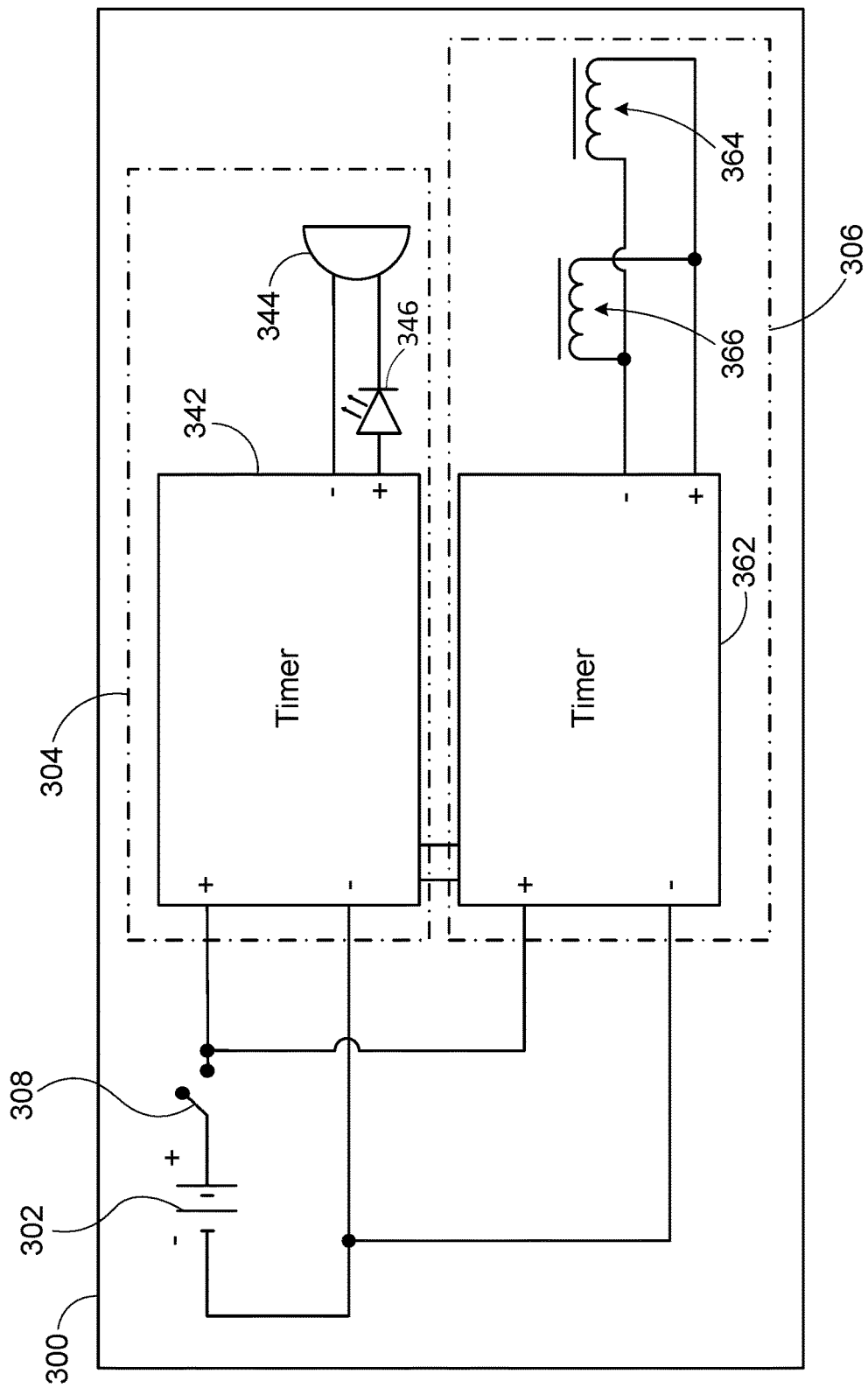
FIG. 4 is a schematic view of an electrical control system for automated ventilation and assisted compression of a patient.

Referring now to FIG. 4, an electrical control system 300 for automated ventilation with assisted compressions of a patient is shown according to one aspect. The system includes a battery 302, an assisted compression mechanism 304, an automated ventilation mechanism 306, and a switch 308. The switch includes an ON and OFF position. In the OFF position, no electricity flows through the circuit. In the ON position, the switch 308 allows electricity to flow from the battery 302 to the assisted compression mechanism 304 and the automated ventilation mechanism 306. In one aspect, the battery 302 is a 12-volt, 350 milliamp-hour, Lithium Polymer battery that can power the system 300 for over 8.5 hours of continuous use.

The assisted compression mechanism 304 includes a timer 342, an audible indicator 344, and a visual indicator 346. The audible indicator 344 and the visual indicator 346 are electrically connected to an output of the timer 342. The timer 342 is configured to output an electrical signal at predetermined intervals indicating when the rescuer is supposed to apply a chest compression. In one aspect, the timer outputs a square-wave pattern at about 100 beats per minute (1.67 Hz). When the electrical signal is output, the audible indicator 344 outputs a sound that can be heard by the rescuer. In one aspect, the audible indicator 344 functions like a metronome by outputting a continuous and regularly repeating sound (or visual) pattern at a regular frequency (e.g., 100 times per minute or 1.67 Hz) simultaneously with the selective actuation of the control valves 104, 108. This can be accomplished, for example, by using a buzzer that outputs a noise of about 90 dB in order to signal to the rescuer when to apply a chest compression. Also, when the electrical signal is output, the visual indicator 346 may output a visual signal that can be seen by the rescuer. In one aspect, the visual indicator 346 is a light emitting diode that signals the rescuer to apply a chest compression. It is also contemplated that only one type of indicator or more than two types of indicators may be used.

The automated ventilation mechanism 306 includes a timer 362, an inspiration control valve 364 and an expiration control valve 366. The timer 362 is configured to output an electrical signal(s) at predetermined intervals to switch the inspiration control valve 364 and the expiration control valve 366 from the OFF state to the ON state. In one aspect, the timer 362 delivers an output signal of about 12 volts in a square wave pattern that causes the control valves 364, 366 to be in the ON state for about 420 ms and the OFF state for about 3.84 seconds. These times may be selected so that the rescuer performs a single chest compression during the ON state and another six chest compressions during the OFF state.

In some aspects, the timers 342, 362 are operatively connected so as to synchronize operation of the assisted compression mechanism 304 and the automated ventilation mechanism 306. It is contemplated that the assisted compression mechanism 304 may be in a system without the automated ventilation mechanism 306. Alternatively, the automated ventilation mechanism 306 may be in a system without the assisted compression mechanism 304. Additionally or alternatively, the assisted compression mechanism 304 and the automated ventilation mechanism 306 may share a single timer.

Referring now to FIGS. 2A-2B, an inspiration and expiration cycle of the system 100 is described. During inspiration the control valves 104, 108 are in the ON position. The expiration control valve 108 applies positive pressure to the downstream side of the exhalation valve 166 in order to keep the exhalation valve 166 from operating. The two inspiration control valves 104 pass gasses from the gas source 102 to the breathing apparatus 106. During the inspiration cycle, the rescuer applies chest compressions to the chest of the patient as guided by the audible or visual indications produced by the indicator 344, 346 at a regular and continuous frequency, such as 100 times per minute. In other words, one or both of the indicators 344, 346 produce the audible (e.g., outputting a brief buzzer sound) or visual (e.g., briefly activating a light-emitting diode) while the control valves 104, 108 are selectively activated to supply gas to the breathing apparatus 106 and allow venting of expired air from a human patient from the breathing apparatus 106 to the atmosphere. After a predetermined period of time, control valves 104, 108 are switched to the OFF state and the expiration cycle begins. While in the OFF state, neither the inspiration control valves 104 nor the expiration control valve 108 transfer gas from the gas supply 102 to the breathing apparatus 106. Further, while in the OFF state, both inspiration control valves 104 and the expiration control valve 108 vent air from the breathing apparatus 106 to the atmosphere. The resulting drop in gas pressure between the expiration control valve 108 and the exhalation valve 166 allows the exhalation valve 166 to operate, allowing for rapid and complete expiration. When no pressure is applied, the lungs of the patient evacuate and force gas through the I-GEL® supraglottic airway device 164 and into the system. The exhaled gas flows through the exhalation valve 166 and the expiration control valve 108 where the exhaled gasses escape to the atmosphere. During the expiration cycle, the rescuer continues to apply chest compressions as guided by the indications produced by the indicator 344, 346 at a regular and continuous frequency. Because the machine automatically switches between the inspiration cycle and expiration cycle without any input from the rescuer, chest compressions may be continuously applied without interruption simultaneously with the operation of the control valves 104, 108.

The systems and methods disclosed herein are generally more effective than conventional MTMV CPR. What is more, the lay public can generally be easily taught to insert an LMA and perform both continuous chest compressions and effective ventilation using aspects of the present disclosure, whereas standard MTMV CPR may be difficult to teach. Further, most rescuers in the lay public cannot properly ventilate a patient using MTMV CPR, and, thus, should perform chest-compression-only CPR to avoid wasting critical time attempting to deliver ventilation that is often ineffective. In an example study, one-third of participants were unable to deliver any successful breaths using MTMV CPR despite having been taught how to perform MTMV CPR using standard AHA training techniques by a certified AHA instructor only minutes before trials were performed. What is more, the average Minute Volume for those that could deliver a successful breath was only about 628 mL, which is not enough to justify the average non-compression time of about 63.43 seconds needed to perform the MTMV CPR.

Further, aspects of the present invention can be used in a wide variety of patients and clinical scenarios from pediatrics to adults because of the variable nature of the volumes and pressures used in ventilation. Average and larger size adults, with normal lung compliance, will generally receive the full tidal volume of about 250 mL because the peak pressure created by ventilation with the system is below the pressure relief valve setting. Smaller patients will trip the relief valve when the desired peak inspiratory pressure is reached, corresponding to the appropriate tidal volume for the size of the patient. Patients with stiff and/or diseased lungs may cause the pressure relief valve to trip before the delivery of a full tidal volume, which is viewed as a benefit and not a limitation of the present disclosure because the pressure relief valve is designed to deliver the maximum tidal volume before dangerous pulmonary barotrauma or gastric distention is created.

The proliferation of Automatic External Defibrillators ("AED") in a growing number of public areas indicates that it is possible to strategically store technological devices in places that can be utilized by the lay public in CPR. Systems according to the present disclosure could similarly be placed in public areas in addition to AEDs. What is more, aspects of the present invention may be combined with typical AEDs in a single system. The combined device would be much smaller and simpler than two separate devices because, for example, many of the components of AEDs could be shared with aspects of the present disclosure.

One example of such a shared component is the voice assist function of many AEDs. This function could be modified to include instructions on LMA insertion and methods associated with the present disclosure in order to further aid lay responders. Software modifications may also be made to provide the metronome feature using the voice assist function of the AED.

Further, aspects of the present disclosure may be modified to inject CPR medications into the trachea through the LMA using pneumatics and a modified AED algorithm. The American Heart Association Advanced Cardiac Life Support protocol is specific about which medications should be injected at what time. A software algorithm can follow the AHA guidelines using the electro cardiogram as a driver, which is already part of the AED. The software of an AED may recognize cardiac rhythm and determine when life supporting medications should be delivered by the system. Gas-pressurized injections of medications, such as epinephrine, can, therefore, be delivered into the trachea by the system via the LMA under complete control of the AED software. This type of AED algorithm design can, for the first time, bring advanced life support techniques to lay-public CPR.

Yet further, aspects of the present disclosure may be modified to include a device that performs automated chest compressions. Automated chest compression devices simulate manual chest compressions by applying mechanical force to the chest of the patient. A variety of mechanisms may be used to accomplish the mechanical chest compressions such as pneumatic vests, load-distributing bands, and actuators including pneumatic or electric-driven pistons. Some such devices include the AUTOPULSE® (Zoll Medical Corporation, Chelmsford, Mass., USA), the LIFE-STAT® device (formerly the THUMPER®) (Michigan Instruments, Grand Rapids, Mich., USA), and the Lund University Cardiac Assist System (LUCAS®) (Jolife AB, Lund, Sweden). Such devices assist in avoiding rescuer fatigue and dwindling compression quality over time. A system incorporating both automated ventilation and automated compression may include, for example, the ventilation system 100 and a modified electrical control system. The modified electrical control system may include, for example, the battery 302, the automated ventilation mechanism 306, and the switch 308. The timer 362 would be synchronized with the compressions from the automated compression device to produce the same ventilation effect as described above.

In some aspects, a system provides a combination of automated ventilation, automatic defibrillations, automated compressions, and automated application of medications. Such a system could be used on a patient to provide continuous, uninterrupted compressions and ventilation to the patient over an extended period of time. The uninterrupted compressions and ventilation could continue during transportation to a hospital. This includes ventilation and chest compressions occurring while moving the patient from the initial location of cardiac arrest to an ambulance, while transporting the patient in the ambulance, and while moving the patient from the ambulance to the hospital. Further, the automatic defibrillation and automatic application of medications allow for advanced resuscitation techniques without unnecessary interruptions to the ventilation or compressions.

Figure 5:
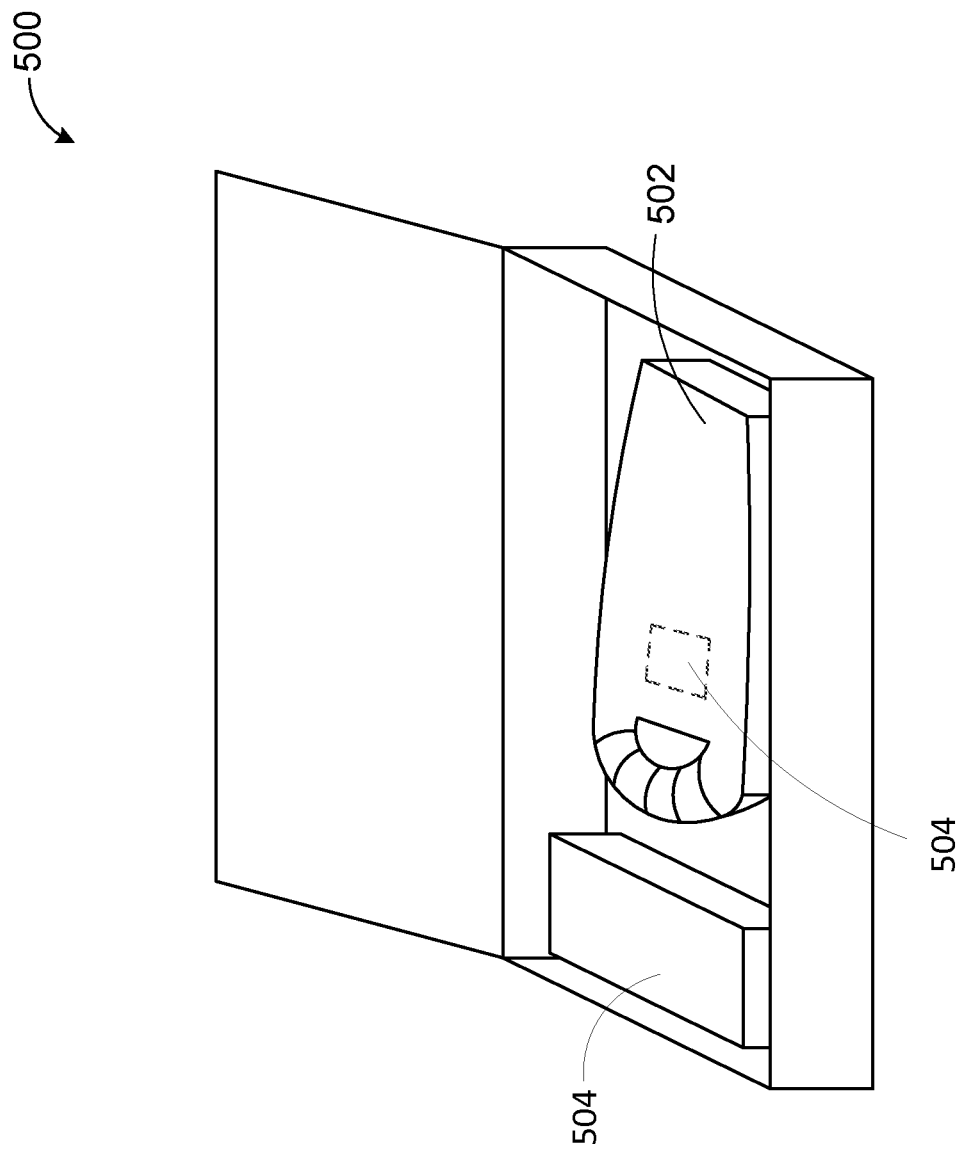
FIG. 5 is a perspective view of a kit of components including an automatic external defibrillator and an indicator.

Referring now to FIG. 5, a kit of components 500 may be provided that includes an AED 502 and an indicator 504 configured to indicate when a chest compression should be performed. The indicator may be, for example, the audible indicator 344 and/or the visual indicator 346. A timer may be included with the indicator 504. The indicator may be included in the AED 502 itself.

Aspects of the present disclosure use pressurized oxygen for ventilation. Alternatively, gas containing lower levels of oxygen can be used when pure oxygen is contraindicated or not desired. For example, firefighters have limited ability to use oxygen in the presence of an ignition source. Lightweight tanks filled with atmospheric air can be used instead of oxygen. Alternatively, a pump can be used to compress air and supply the system with air as-needed.

Additionally, aspects of the present disclosure can be used to deliver electrical shock for cardiac defibrillation. For example, one of the two external pads used for cardiac defibrillation by the AED may be replaced by aspects of the present disclosure such as the LMA. The LMA would be modified to carry a charge to a desired location within the patient. The internal placement of the LMA and the preferred contact with an internal mucosal membrane holds promise of dramatically improved electrical contact and effectiveness, which may result in increased effectiveness of defibrillation or lower power needed.

In some aspects, the system can be modified to monitor chest compressions in order to determine whether the chest compressions are adequate and/or properly timed. In one nonlimiting example, a sensor monitors air pressure proximate to the respiratory system of the patient. A chest compression generally increases intrathoracic pressure and, similarly, increases measured air pressure of the respiratory system. This rise can be compared to a baseline or calibration curve to determine the adequacy and/or timing of the compression. In another nonlimiting example, the system includes a pressure sensor disposed between the chest of the patient and the hands of the rescuer. The pressure sensor can be used to determine, for example, the adequacy and/or timing of the compression. In yet another nonlimiting example, the system may include an accelerometer disposed, for example on a hand of the rescuer, to determine the adequacy and/or timing of the chest compression.

A system with monitored chest compressions can be further modified to include a dynamic indicator. For example, the indicator could signal inadequate chest compressions by providing a different audio and/or visual signal, becoming louder, showing an alternate color, and/or using a voice command to inform the rescuer to apply more force with compressions.

Aspects of the present disclosure can be modified to deliver a wide variety of ventilation modes. This includes modification of tidal volume, pressure relief, and respiratory rate to meet the specific needs of many situations, even when cardiac arrest is not an issue. For example, firefighters or Emergency Medical Services can use systems and methods of the present disclosure for emergency transport during extraction or in field applications where a lightweight ventilator is important.

EXAMPLES

Endpoint variables were measured to compare the lay public's effectiveness in conventional MTMV CPR and CPR using an Example System according to the present disclosure, including: (1) volume of ventilation per minute ("Minute Volume"); (2) Minute Volume after accounting for dead-space ventilation; (3) total period without chest compressions; (4) total number of chest compressions; (5) rate of chest compressions; (6) time to first compression; and (7) time to first ventilation. Further, the lay public's self-reported preferences between MTMV CPR and the automated ventilation and assisted compression system were recorded.

The example system was designed to administer breaths with an inspiration time (I-Time) as short as the downward chest compression phase. At about 100 compressions per minute, this inspiration time is approximately 400 milliseconds. The I-GEL® supraglottic airway device has a maximum recommended peak pressure of approximately 26 cm $H_2O$. Because of short the I-Time and maximum peak pressure, the example system delivers frequent, low-tidal-volume (Vt) breaths.

The Anatomic Dead Space is the total volume of the airway tract leading from the patient's mouth and nose to the alveoli in the lungs. In an adult male, this dead space is approximately 150 mL. The dead space volume must be subtracted from the total tidal volume when calculating how much air actually reaches the patient's alveoli to participate in gas exchange. When MTMV CPR is performed according to AHA standards, the effective Minute Volume is approximately 1.4 L plus dead space. This volume includes expired air with a fraction of inspired oxygen of about 15%. The example system was designed to administer the AHA standard effective Minute Volume of about 1.4 L. However, the example system delivers a fraction of inspired oxygen of about 100% and, thus, provides approximately 6.67 times more oxygenation than properly-performed MTMV CPR.

The example system was tested to determine parameters needed to supply the effective Minute Volume using tidal volumes delivered in less than about 400 milliseconds with less than about 26 cm $H_2O$ peak inspiratory pressure. The variables that were manipulated to accomplish this included oxygen supply pressure, number of pneumatic valves, diameter of ventilation circuit, supply valve orifice, inspiratory time, and relief valve pressure setting. The goal was to determine settings that delivered the largest tidal volume within about 400 milliseconds while maintaining peak pressures below about 26 cm $H_2O$.

Figure 6:
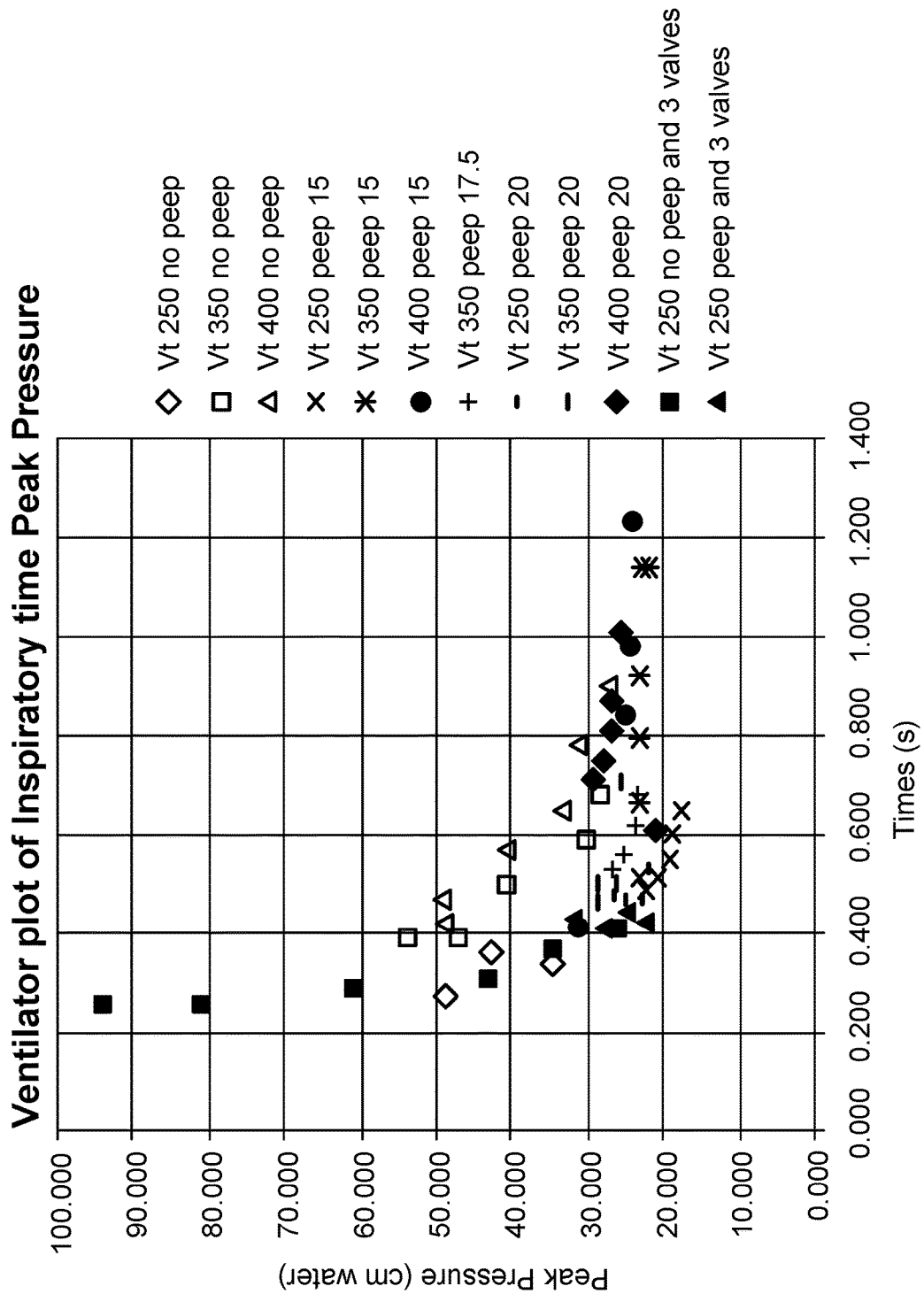
FIG. 6 is a graph depicting optimization of the peak pressure applied versus inspiratory time for systems varying several parameters.

FIG. 6 illustrates the results of sixty different trials performed using different combinations of the above variables with multiple tests being performed for each combination of dependent variables. "Vt" indicates the tidal volume, and "peep"/"no peep" indicates whether Positive End-Exhalation Pressure (e.g., a relief valve) was used. All of the systems included two solenoid valves unless indicated to include "3 valves." For example, the hollow squares labeled "Vt 350 no peep" indicate that the tidal volume was 350 mL, that no pressure relief valve was used, and that two solenoid valves were used (one inspiration, one expiration). The solid squares labeled "Vt 250 no peep and 3 valves" indicate that the tidal volume was 250 mL, that no pressure relief valve was used, and that three solenoid valves were used (two inspiration, one expiration). The supply pressures tested ranged from about 40 psi to about 110 psi. Measurements of ventilation volume, flow, pressure, inspiratory time, and expiratory time were taken with a MALLINCKRODT PURITAN BENNET BREATHLAB PTS-2000 VENTILATOR ANALYZER™ (Mallinckrodt Group, Hazelwood, Mo.).

As shown in FIG. 6, the Example System including three solenoid-controlled pneumatic valves (two for inspiration, one for expiration), a spring-controlled pressure relief valve set to about 20 cm $H_2O$, and a tidal volume of about 250 mL delivered in about 420 ms produces peak inspiratory pressures of approximately 23 cm $H_2O$. Assuming a normal adult dead-space volume of about 150 mL, the effective ventilation will be about 100 mL per breath. Thus, an effective minute ventilation of about 1.4 L required a respiratory rate of about 14 breaths per minute.

Once the number of breaths per minute was determined, the ventilation and chest compressions were synchronized. The built-in metronome feature was designed to sound at about 100 beats per minute. The inspiratory phase was synchronized with the metronome feature to deliver positive-pressure breaths during the downward chest compression phase. This generally increased intrathoracic pressure during the chest compression and enhanced the effectiveness of chest compressions. Also, this synchronization minimized the negative effect of ventilation on venous return to the heart during the decompression phase of chest compressions. Using this information, the Example System was set to deliver one breath for every seven chest compressions. This rate provided the required fourteen breaths in slightly less than one minute.

An additional benefit of the Example System is that it is lightweight, compact, and portable. The main module used in the present example measured about 4 inches (10.16 cm) by about 2 inches (5.08 cm) by about 6 inches (15.24 cm) and it weighed only about 28.6 ounces (810.8 g). This was the smallest and most lightweight ventilator at the time it was built. This lightweight and compact design makes the Example System ideal for transport, storage, and use by rescuers. Further, the example ventilator was the only ventilator that functions with a simple on/off switch. This makes the system incredibly easy to use, especially for the lay public.

The Example System was tested using 44 participants from the lay public, including 18 men and 26 women. The education levels of the sample group are detailed in Table 1.

TABLE 1

Education Achieved

| Education Achieved | Frequency | Percent | Cumulative Percent |
|---|---|---|---|
| Currently in High School | 11 | 25.0 | 25.0 |
| Completed High School | 5 | 11.4 | 36.4 |
| 2-Year College | 3 | 6.8 | 43.2 |
| 4-Year College | 16 | 36.3 | 79.5 |
| Graduate School | 9 | 20.5 | 100.0 |
| Total | 44 | 100.00 | 100.0 |

The age range of the subjects was 14-60 (mean 37+/−15.0). Persons both certified in CPR (n=12) and not certified in CPR (n=32) were accepted into the study. Subjects were screened for physical capabilities per the AHA guidelines before their participation in the study. The screening process informed subjects of the physical exertion required during CPR and asked them to disclose any information that may hinder their ability to participate. No subjects were eliminated.

Measurements were taken using a LAERDAL® SIM-MAN® (Laerdal Medical, Stavanger, Norway) manikin patient simulator. The pulmonary system of the manikin was upgraded using a MAQUET® 190 (Maquet Medical Systems, Wayne, N.J.) Adult Test Lung to simulate human lung compliance of about 20 cm $H_2O$ and allow for accurate tidal volume measurements. Additionally, the manikin was modified to include a MALLINCKRODT PURITAN BENNET BREATHLAB PTS-2000 VENTILATOR ANALYZER™ (Mallinckrodt Group, Hazelwood, Mo.), which continuously measured tidal volumes and pulmonary pressure. To capture all other variables, subjects were videotaped allowing for later analysis of time to first ventilation, time to first compression, total time of no compressions, total number of compressions, and compression rate.

Subjects were taught MTMV CPR and automated ventilation and assisted compression CPR using instruction and practice videos. In both teaching scenarios, subjects had the ability to ask the instructor any questions pertaining to their CPR attempts. A placebo ventilator was also utilized that was similar to the Example System, but applied a different ventilation pattern and lacked a metronome feature. The placebo teaching and trial phase was always performed after use of the Example System to avoid skewing the Example System's results through prior practice with the I-GEL® supraglottic airway device.

Time began when the subject first touched the manikin or the airway device. Subjects were asked to perform CPR for 3 minutes for each of the three methods tested. The tidal volume of each breath was recorded in order to calculate the average Minute Volume and average non-dead space Minute Volume for all three minutes. The time to first ventilation was the time until the first breath greater than about 150 mL was delivered. The rate of chest compressions was calculated by dividing the total number of compressions in three minutes by the total time used to perform chest compressions.

The subjects also completed a survey to assess participant preferences after all trials were performed. These preferences included satisfaction with each technique, difficulty using each technique, likelihood of performing each technique, preference ranking, protection from body fluids, and importance of the metronome feature.

The primary endpoint variables and the post-survey preference results were compared using the Wilcoxon Signed Ranks test, a nonparametric counterpart to the paired t-test. Alpha was set at 0.01, instead of the usual 0.05, because several analyses were performed. This "Bonferroni-type" adjustment was applied because it is more likely to find a significant difference at the nominal 5% level when one does not actually exist with this number of statistical tests. In order to determine the variation in compression rates between the groups, the coefficient of variation (CV) was computed for both methods.

The endpoint variables are described in Table 2 below.

TABLE 2

Endpoint Variables

| Variable | MTMV CPR | Example System | P-Value |
|---|---|---|---|
| Minute Ventilation (L) | 0.628 ± 0.684 | 4.064 ± 0.620 | P < 0.001 |
| Non Dead Space Minute Ventilation (L) | 0.314 ± 0.516 | 2.126 ± 0.533 | P < 0.001 |
| Time to first ventilation (seconds) | 94.11 ± 75.93 | 6.70 ± 2.47 | P < 0.001 |
| Total number of compressions | 200 ± 19 | 286 ± 7 | P < 0.001 |
| Time to first compression (seconds) | 0.00 ± 0.00 | 8.95 ± 3.10 | P < 0.001 |
| Total time of no Chest Compression (seconds) | 63.43 ± 7.39 | 8.82 ± 2.79 | P < 0.001 |

As shown, all measured endpoint variables were statistically significant. Subjects were able to provide significantly more total Minute Volume and non-dead space Minute Volume using the Example System than with MTMV CPR (p<0.001). The average Minute Volume for MTMV CPR was only about 628 mL compared to more than about 4000 mL with the Example System. Surprisingly, seventeen participants were completely unable to provide any successful breaths using MTMV CPR while the Example System provided successful ventilation during all trials.

What is more, subjects were able to limit the total time of no chest compressions to an average of about 8.8 seconds when using the Example System rather than the about 63.4 seconds with MTMV CPR (p<0.001). When using the Example System, subjects were able to provide an average of about 286 chest compressions during the three minute trials compared to only about 200 chest compressions with MTMV CPR (p<0.001). This is an increase of about 43%.

Because so many participants were unable to provide successful breaths using MTMV CPR, the average time to first ventilation was about 94.11 seconds with MTMV CPR compared to only about 6.70 seconds with the Example System (p<0.001).

Figure 7:
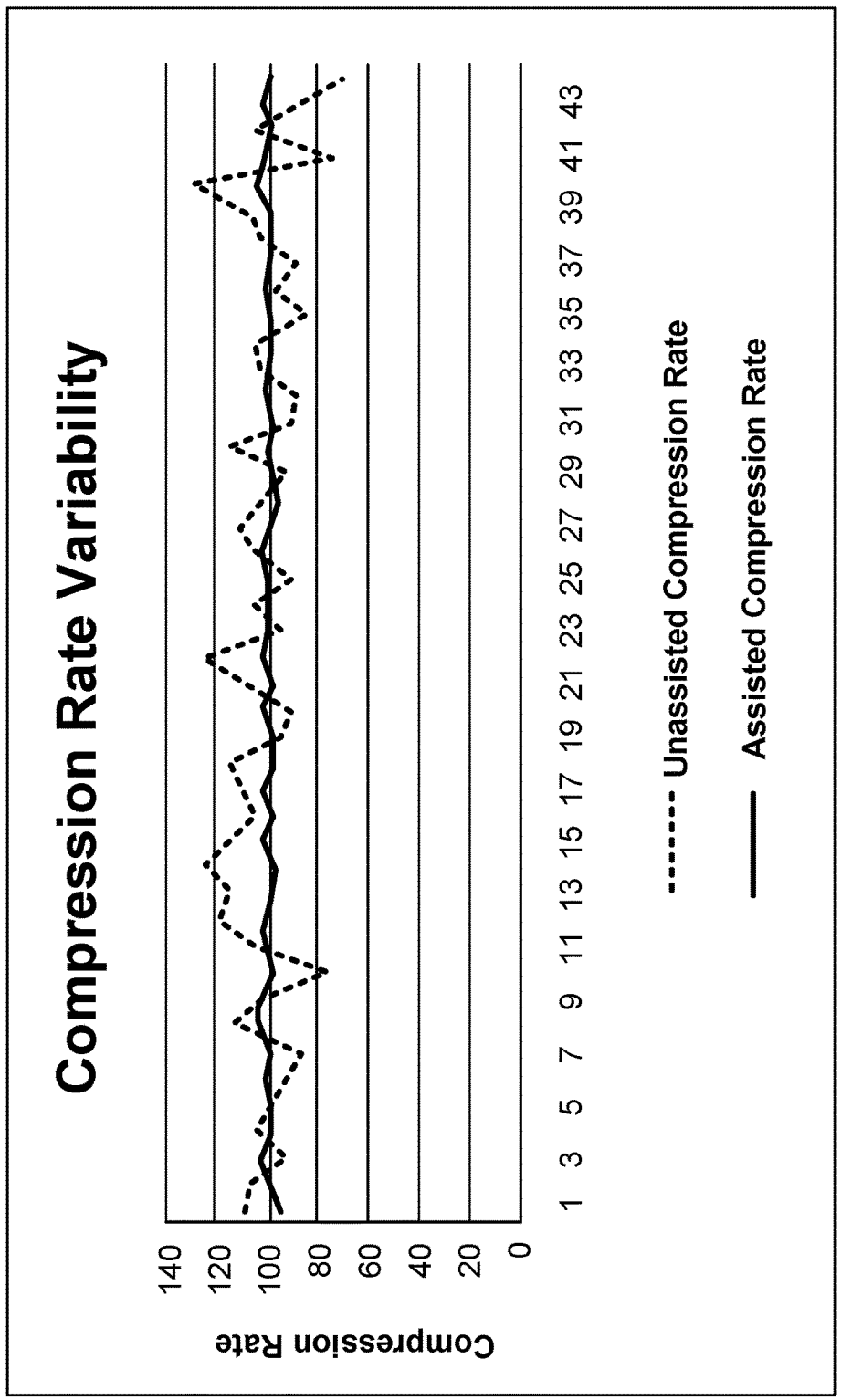
FIG. 7 is a graph depicting the average compression rate by test subject using unassisted compressions and metronome-assisted compressions.

Referring now to FIG. 7, a graph depicting the average compression rate by test subject using unassisted MTMV CPR and using the Example System is shown. Both average rates were within the AHA guidelines of 100 chest compressions per minute; however, the average standard deviation for MTMV CPR is about 13.01 compressions per minute, while the standard deviation for the metronome-assisted compressions is only about 2.00 compressions per minute. Notably, during MTMV CPR, sixteen participants performed compressions at a rate significantly below the AHA recommended standard. The slowest rate was equal to about 72.6 chest compressions per minute. In contrast, no one using the Example System performed chest compressions at a rate significantly below the AHA standard. Further, the coefficient of variation was about 12.7% with MTMV CPR versus only about 2% with the Example System. Thus, use of the metronome feature provided greater consistency around the desired rate than MTMV CPR (p<0.001).

The time to first chest compression was shorter (p<0.001) with MTMV CPR than with the Example System. This is because MTMV CPR always begins with chest compressions. However, the average time to first chest compression was only about 8.95 seconds with the Example System. This difference is not significant and is far outweighed by the other benefits provided by the Example System.

Further, as shown in Tables 3A and 3B below, the self-reported survey results show that Example System was preferred to MTMV CPR in all five categories (p<0.001). The categories included satisfaction, ease of use, likelihood to use, rank, and protection from body fluids. The subjects rated satisfaction, ease of use, and likelihood to use on a scale from 1 to 5, 1 being the best (e.g., 1-very satisfied with the airway technique and 5-very dissatisfied with airway technique). The subjects rated the order of preference from 1-3, 1 being the best. The subjects were also asked to rate the helpfulness of the metronome feature. About 95.5% of subjects rated the metronome feature helpful to very helpful. The other about 4.55% were indifferent. No one reported that the metronome feature was detrimental to adequate chest-compression timing. Numbers on the tables below represent the average rating given (1-5 for satisfaction, ease of use, likelihood of use; 1-3 for order of preference) and percentages are based on the number of participants selecting a given option.

TABLE 3A

Preferences and Perceptions

|  | MTMV CPR | Example System CPR | Placebo CPR | P-Value |
|---|---|---|---|---|
| Satisfaction | 2.59 | 1.40 | 2.01 | P < 0.001 |
| Ease of use | 2.69 | 1.31 | 2.00 | P < 0.001 |
| Likely to use | 2.73 | 1.45 | 1.82 | P < 0.001 |
| Order of preference | 2.75 | 1.31 | 1.94 | P < 0.001 |
| Protection from body fluids | 0.0% | 100% believed the Example System or Placebo provided better protection | | P < 0.001 |

TABLE 3B

Preferences and Perceptions

|  | MTMV CPR | Example System | Placebo system |
|---|---|---|---|
| Satisfied or very satisfied | 31.8% | 100% | 68.2% |
| Easy or very easy to use | 18.2% | 93.2% | 59.1% |
| Very probably or definitely likely to use | 31.8% | 95.5% | 70.5% |
| Ranked first as preferred technique in actual CPR | 6.8% | 70.5% | 22.7% |
| Most likely to protect from body fluids | 0.0% | 100% believed either the Example System or Placebo provided better protection | |
| Metronome is helpful or very helpful | | 95.5% | |

Subjects in this study were able to deliver over six times more Minute Volumes, over seven times more non-dead space ventilation, 44% more chest compressions, an almost eight-fold reduction in wasted non-compression time, and a fourteen-fold reduction in the time required to deliver a first successful breath when performing CPR with the Example System compared to MTMV CPR. All results were found to be statistically significant, as shown above. Moreover, favorable endpoint variables discussed above only improve the longer CPR is performed. Out-of-hospital CPR is almost always much longer than the example time used, making the value of the Example System even more pronounced. For example, the average total time of no chest compressions is about 21 seconds for every minute of CPR in the MTMV CPR group. In stark contrast, the average total time for no chest compressions using the Example System is only about 8.9 seconds, regardless of how long CPR is performed.

The Example System was set to deliver fourteen 250 mL breaths per minute, or a Minute Volume of about 3.5 L. Surprisingly, the testing showed that the Minute Volume for the Example System was an average of about 4.06 L per minute; an additional about 506 mL of ventilation. This increase was created by passive ventilation resulting from the effects of chest compressions on the lung. What is more, this effect was only seen during ventilation with the Example System because the I-GEL® supraglottic airway device maintained the airway and allowed for passive air movement during chest compressions. This was an unexpected positive finding, further supporting the value of aspects of the present disclosure.

The foregoing specific embodiments of the present invention as set forth in the specification herein are for illustrative purposes only. Various deviations and modifications can be made within the spirit and scope of this invention, without departing from the main theme thereof. It will be appreciated by persons skilled in the art that the present invention is not limited by what has been particularly shown and described herein above.

The invention claimed is:

1. A lightweight, compact, and portable apparatus to facilitate simultaneous ventilation and resuscitation of a patient, the apparatus comprising:
an inspiration control valve disposed downstream of an oxygen source having a gas that includes oxygen;
a connector configured to interface with a supraglottic airway device disposed downstream from the inspiration control valve, the supraglottic airway device configured to form an air seal such that the gas including oxygen can flow from the oxygen source through the connector;

an expiration control valve configured to selectively actuate a one-way exhalation valve;
an indicator providing a rate of at least 100 audio, visual, or audiovisual indications per minute;
a pressure relief valve between the inspiration control valve and the suppraglottic airway device, the pressure relief valve being configured to actuate and release gas if pressure at the pressure relief valve increases beyond a predetermined threshold so as not to exceed a peak inspiratory pressure of 26 cm $H_2O$ relative to atmospheric pressure;
a control system, configured to:
selectively open the inspiration control valve to allow the gas to flow from the oxygen source to the airway device for about 400 to 420 ms during an inspiration cycle and then close the inspiration control valve while simultaneously opening the expiration control valve to allow one-way venting of air from the airway device to the atmosphere during an expiration cycle, at a rate of less than 15 times per minute while the pressure relief valve is controlled to ensure that the peak inspiratory pressure does not exceed 26 cm $H_2O$ relative to atmospheric pressure so as to deliver to the patient a tidal volume corresponding to at least the patient's size or the patient's lung condition without creating a pulmonary barotrauma or a gastric distension condition in the patient, wherein the selectively opening and closing of the inspiration and expiration control valves is synchronized with the indications,
a timer configured to synchronize the actuation of the inspiration control valve and the expiration control valve; and
a switch configured to activate the timer such that in response to actuating the switch, the apparatus begins to automatically switch between the inspiration cycle and the expiration cycle without any further external input to the apparatus;
wherein the lightweight, compact, and portable apparatus has a weight that does not exceed about 28.6 ounces.

2. The apparatus of claim 1, further including the oxygen source, the oxygen source being an oxygen tank that is lightweight, compact, and portable, such that the apparatus together with the oxygen tank form a system that is lightweight, compact, and portable.

3. A kit of components for assisting in resuscitation of a patient, the kit comprising the apparatus according to claim 1 in combination with an Automatic External Defibrillator.

* * * * *